(12) United States Patent
Myers

(10) Patent No.: US 9,592,372 B2
(45) Date of Patent: Mar. 14, 2017

(54) LINKAGE ACTUATED HEMOSTASIS MECHANISM AND METHOD

(71) Applicant: Cook Medical Technologies LLC, Bloomington, IN (US)

(72) Inventor: Randy Joe Myers, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 285 days.

(21) Appl. No.: 14/327,621

(22) Filed: Jul. 10, 2014

(65) Prior Publication Data

US 2015/0112279 A1    Apr. 23, 2015

Related U.S. Application Data

(60) Provisional application No. 61/893,324, filed on Oct. 21, 2013.

(51) Int. Cl.
*A61M 5/14*        (2006.01)
*A61M 39/06*      (2006.01)

(52) U.S. Cl.
CPC ... *A61M 39/0613* (2013.01); *A61M 2039/062* (2013.01); *A61M 2039/0673* (2013.01)

(58) Field of Classification Search
CPC .... A61M 2039/0673; A61M 2039/062; A61M 25/0693; A61M 39/0613
USPC .................................................. 604/256, 250
See application file for complete search history.

(56) References Cited

U.S. PATENT DOCUMENTS

| | | | | |
|---|---|---|---|---|
| 4,612,010 A | * | 9/1986 | Hamacher | A61M 5/315 222/340 |
| 5,161,773 A | * | 11/1992 | Tower | A61M 39/0613 251/5 |
| 2004/0172008 A1 | | 9/2004 | Layer | |
| 2013/0006176 A1 | * | 1/2013 | Miller | A61M 25/1018 604/97.02 |

* cited by examiner

*Primary Examiner* — Edelmira Bosques
(74) *Attorney, Agent, or Firm* — Liell + McNeil

(57) ABSTRACT

A hemostasis mechanism includes a deformable seal, and a plunger guided for translation within a housing to displace a fluid to a clearance extending between the deformable seal and the housing. The displaced fluid increases fluid pressure in the clearance to deform the deformable seal into sealing contact with a medical device. An actuator for the plunger includes a linkage having arms rotatable about first and second axes, and configured such that their rotation is converted into translation of the plunger. The linkage is adjustable from a retracted configuration to an advanced, cammed-over configuration.

19 Claims, 2 Drawing Sheets

LINKAGE ACTUATED HEMOSTASIS MECHANISM AND METHOD

TECHNICAL FIELD

The present disclosure relates generally to fluidly sealing about a medical device in a hemostasis mechanism, and relates more particularly to actuating a plunger for controlling a deformable seal in a hemostasis mechanism, via rotation of arms in a mechanical linkage.

BACKGROUND

A variety of different sealing mechanisms are used to prevent the backflow of blood or other fluids from a patient during certain types of treatment or diagnostic procedures. In a typical transluminal treatment or diagnostic scenario, a clinician controls such a mechanism to alternately block or open a fluid conduit extending from outside the patient into an intraluminal space such as a vein or artery. Transluminal devices such as wire guides and catheters may be passed through the conduit when open, and backflow of blood or another fluid can be prevented when the conduit is closed. Since it is often necessary for transluminal devices to reside within the fluid conduit when a seal is established, many sealing mechanisms are engineered to fluidly seal around a wire guide, catheter or the like.

One particular strategy employs a push/pull sleeve or tube, coupled with a housing, which can be advanced through the center of a resilient gasket or the like positioned in the housing to open the gasket and provide a passage for introducing a transluminal device into the patient. When the push/pull sleeve is retracted, a fluid seal is formed about the device by way of a tendency for the gasket to return to a closed state. Other techniques employ a rotating mechanism which adjusts a different type of gasket from an open configuration to a closed configuration, sealing about a transluminal device. Each of these strategies has various drawbacks. In the case of rotating mechanism devices, their use can be unwieldy and slow. In certain instances, a clinician may need to seal and unseal about a device multiple times during a procedure, and the need to rotate a sealing mechanism to seal, unseal, seal again, etc. can be tiresome. In the case of push/pull devices, some of these shortcomings do not exist, as forming or un-forming a seal is fairly quick and easy. A tradeoff may exist, however, in the robustness of the seal, for at least certain of such designs. In other words, while push/pull designs may be efficient to use, the seal may not be as effective against preventing backflow of fluid from a patient.

Another known strategy is set forth in United States Patent Application Publication Number 2004/0172008 to Layer. Layer proposes a hemostasis valve having a collapsible member positionable within a valve body, and a pressure application system configured to increase a pressure within an elongate chamber in the valve body to seal the collapsible member about a medical instrument. While Layer may be suitable for its intended purposes, the strategy has various shortcomings.

SUMMARY OF THE DISCLOSURE

In one aspect, a hemostasis mechanism includes a housing having an outer surface, and an inner surface defining a through-bore having a longitudinal axis, and a deformable seal extending circumferentially around the longitudinal axis and being positioned within the through-bore. A clearance extends between the deformable seal and the inner surface. The mechanism further includes a plunger guided for translation within the housing from a first position to a second position to displace a fluid to the clearance, such that a fluid pressure in the clearance is increased to deform the deformable seal into sealing contact with a medical device within the through-bore. The mechanism further includes an actuator for the plunger including a linkage having a first arm rotatable about a first axis relative the housing, and a second arm rotatable about a second axis relative the first arm and being coupled to the plunger, such that rotation of the first arm is converted via rotation of the second arm into translation of the plunger between the first and second positions.

In another aspect, a method of fluid sealing about a medical device in a hemostasis mechanism includes rotating arms of a linkage coupled with a plunger within a housing of the hemostasis mechanism, such that the plunger is translated in response to the rotation from a first position toward a second position. The method further includes increasing fluid pressure within a clearance extending between the seal and the housing via fluid displaced via the translation of the plunger. The method still further includes deforming the seal into sealing contact with a medical device extending through the housing, in response to the increased fluid pressure.

DETAILED DESCRIPTION

Figure 1:
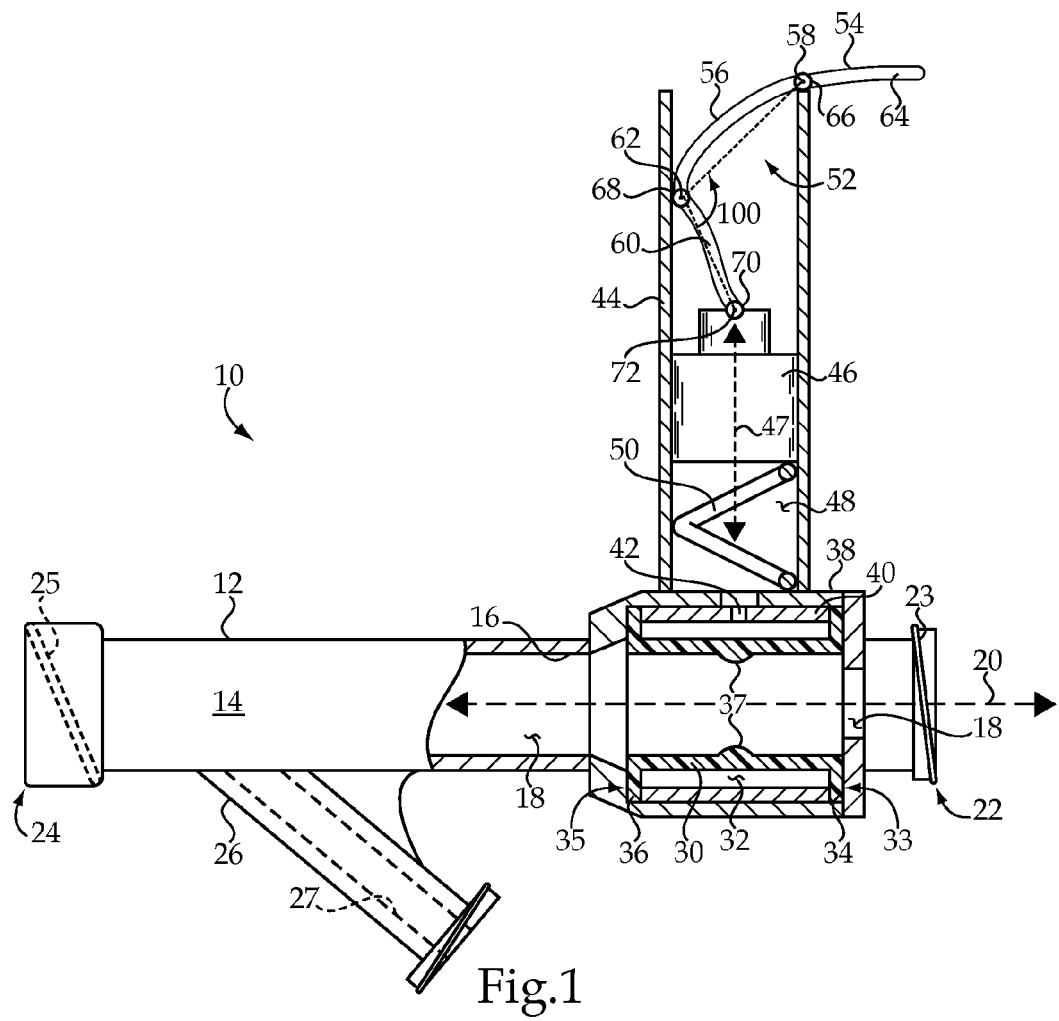
FIG. 1 is a partially sectioned side diagrammatic view of a hemostasis mechanism, according to one embodiment.

Referring to FIG. 1, there is shown a hemostasis mechanism 10 according to one embodiment, and including a housing 12 having an outer surface 14, and an inner surface 16 defining a through-bore 18 having a longitudinal axis 20. Housing 12 includes a proximal housing end 22 which includes a fitting 23, and a distal housing end 24 including another fitting 25. In one practical implementation strategy, fitting 23 includes a male luer and fitting 25 includes a female luer. Housing 12 may further include a sidearm 26 defining a passage 27 which connects with through-bore 18 for purposes of injecting fluid or introducing a medical device into a patient. A deformable seal 30 is positioned within housing 12 and at least partially within through-bore 18, and extends circumferentially around axis 20. A clearance 32 extends between deformable seal 30 and inner surface 16 and may likewise extend circumferentially around axis 20. As will be further apparent from the following description, mechanism 10 is uniquely configured for deforming seal 30 into sealing contact with a medical device extending through through-bore 18.

Seal 30 may include a proximal seal end 33 having a radially projecting flange 34, and a distal seal end 35 also having a radially projecting flange 36. Between flanges 34 and 36 seal 30 may be substantially cylindrical, and having inwardly protruding sealing elements 37. Overall, seal 30 may be generally spool shaped, although the present disclosure is not thusly limited. Seal 30 may be formed from any suitable material such as a silicone material. Housing 12 may be constructed of multiple housing pieces, formed of molded elastomeric materials for instance, and in the illustrated embodiment includes an outer housing piece 38 and an inner housing piece 40. Flanges 34 and 36 may be positioned such that they abut opposite ends of inner housing piece 40 and are clamped via assembly of mechanism 10 to form fluid seals against inner housing piece 40, fluidly sealing clearance 32 but for a port 42 extending through outer housing piece 38 and inner housing piece 40.

Housing 12 may further include a plunger housing piece 44 attached to outer housing piece 38. A plunger 46 is guided for translation within plunger housing piece 44 from a first position to a second position to displace a fluid from a cavity 48 to clearance 32 via port 42, such that a fluid pressure in clearance 32 is increased to deform seal 30 into sealing contact with a medical device within through-bore 18. Mechanism 10 further includes an actuator 52 for plunger 46, including a linkage 54. Linkage 54 includes a first arm 56 rotatable about a first axis 58 relative housing 12, and a second arm 60 rotatable about a second axis 62 relative first arm 56 and coupled to plunger 46. Rotation of first arm 56 about axis 58 is converted via rotation of second arm 60 about axis 62 into translation of plunger 46 between its first and second positions. A handle 54 may be coupled to or be part of first arm 56 to enable a user to rotate first arm 56 in the manner described herein. A fluid within cavity 48 which is displaced to clearance 32 may include a liquid such as saline, but could and typically will instead be a gas such as air. Both liquid and gas could be displaced in certain instances. A biaser such as a biasing spring 50 may also be positioned within housing 12 between plunger 46 and housing piece 38 and opposes translation of plunger 46 toward its second position. It will also be appreciated that in versions where cavity 48 and clearance 32 contain gas translation of plunger 46 toward its second position may also or alternatively be opposed via a compression of the air. Plunger 46 defines an axis of reciprocation 47 which in the illustrated embodiment is oriented normal to axis 20, but might be oriented diagonally or even parallel to axis 20 in other embodiments. Embodiments can thus be readily contemplated where plunger 46 reciprocates in a path parallel and adjacent to through-bore 18.

In the illustrated embodiment, linkage 54 includes a first hinge 66 that couples first arm 56 to housing 12 and defines first axis 58. Linkage 54 may also include a second hinge 68 coupling second arm 60 to first arm 56 and defining second axis 62. A third hinge 70 may couple second arm 60 to plunger 46 and defines a third axis 72. In one practical implementation strategy first axis 58 may have a fixed location relative housing 12, and second axis 62 may have a floating location relative housing 12. This feature may be understood to mean that regardless of the configuration assumed by linkage 54, a location of axis 58 will remain the same. A location of axis 62, however, will vary relative housing 12 dependent upon the angular orientation of arm 56 about axis 58 and is thus a floating location. It may also be noted from FIG. 1 that axis 58 and axis 62 are spaced a fixed distance apart. Axis 68 and axis 70 are likewise spaced a fixed distance apart. As plunger 46 translates, a distance between axis 58 and axis 70 will change, and increase as plunger 46 is advanced from its first position toward its second position. In a practical implementation strategy, each of arms 56 and 60 might be rigid with axis 62 occupying a location at intersecting ends of the arms. In an alternative embodiment, one or both of arms 56 and 60 might be non-rigid, and configured to flex during actuation of linkage 54. By way of flexion of one of arms 56 and 60, and likely arm 60, a point of rotation of arm 60 relative arm 56 might change as linkage 54 moves between a retracted configuration as shown in FIG. 1, and an advanced configuration. In such an embodiment, a location of axis 62 relative axis 58 might change. It is contemplated that conventional mechanical hinges formed by mating parts of arms 56 and 60 and such that the distance between axes 58 and 62 is fixed will nevertheless be a practical implementation strategy. A hinge pin or the like separate from or formed integrally might be used to form hinge 68 and couple arm 56 and arm 60 together, as may analogously be the case with hinges 66 and 70 as well.

Figure 2:
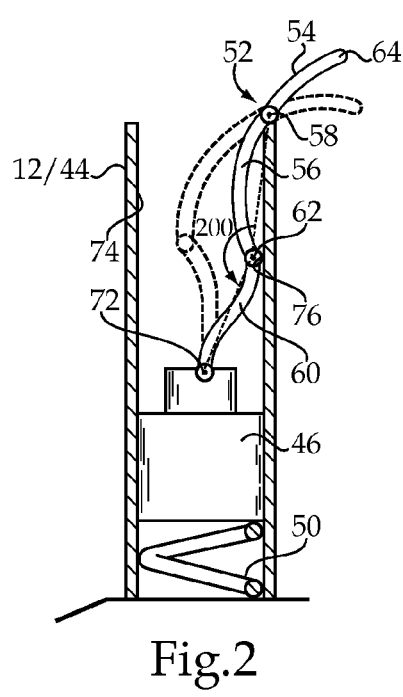
FIG. 2 is a partially sectioned side diagrammatic view of a part of the mechanism of FIG. 1.

As noted above, linkage 54 may be movable from a retracted configuration corresponding to the first position of plunger 46 and illustrated in FIG. 1 to an advanced configuration corresponding to the second position of plunger 46. Referring also now to FIG. 2, in FIG. 1 linkage 54 is shown in the retracted configuration where first axis 58, second axis 62 and third axis 72 define a first included angle 100. When adjusted to an advanced configuration as shown in FIG. 2, first axis 58, second axis 62 and third axis 72 define a second included angle 200. By virtue of adjusting linkage 54 from its retracted configuration to its advanced configuration, linkage 54 may be lengthened, and the lengthening of linkage 54 may correspond generally to a distance which plunger 46 is translated from its first position to its second position. It may further be noted that first angle 100 and second angle 200 may be understood as opposite included angles, and to adjust linkage 54 from the retracted configuration to the advanced configuration linkage 54 may be adjusted past a point at which axes 58, 62 and 72 are positioned in a single straight line. This feature enables linkage 54 to be cammed-over from the retracted configuration of FIG. 1 to the advanced configuration of FIG. 2. Just prior to reaching the advanced, cammed-over configuration linkage 54 may modestly retract, in other words having passed the point at which axes 58, 62, and 72 are in a straight line axes 58 and 72 may draw closer together as angle 200 is assumed. In FIG. 2 linkage 54 is shown in phantom as it might appear approximately half-way between the retracted configuration and the advanced configuration.

It will be recalled that a biaser such as biasing spring 50, and potentially compressible gas occupying cavity 48 and clearance 32, may oppose the translation of plunger 46 toward its second position. Accordingly, when linkage 54 is at a maximally extended configuration where axes 58, 62 and 72 define a single straight line, linkage 54 may be relatively unstable by virtue of the tendency for hinges 66, 68 and 70 to rotate. Absent an external force applied to linkage 54, from an unstable state linkage 54 will tend to rotate back towards either its refracted configuration or its advanced configuration under the influence of the biasing force. Housing 12 may include a first stop 74 and a second stop 76. Contact between linkage 54 and first stop 74 may prevent linkage arms 56 and 60 from further rotation from the retracted configuration, in other words limiting how small included angle 100 can become. Housing 12 may also include another stop 76, and linkage 54 will tend to be locked in the advanced configuration in contact with stop 76 via the biasing force, whether the biasing force is from compressed gas, biasing spring 50, or both. Analogy may be recognized between the properties of mechanism 10 which advantageously exploit camming-over phenomena and properties of other mechanical linkage systems where camming-over is considered problematic or leads to failure.

Such properties of the present disclosure obviate the need for mechanical locking devices, detents or the like which are used in other hemostasis mechanisms and elsewhere in the medical device arts. It is nevertheless contemplated that a positive locking mechanism such as a movable lever or stop which selectively locks handle 64, for instance, could be used in addition to or instead of camming-over without departing from the present disclosure. Where deformable linkage components, such as flexible arms in the embodiments noted above, are used such a linkage could still be understood to be capable of being cammed-over as that term is intended to be understood herein.

Industrial Applicability

Figure 3:
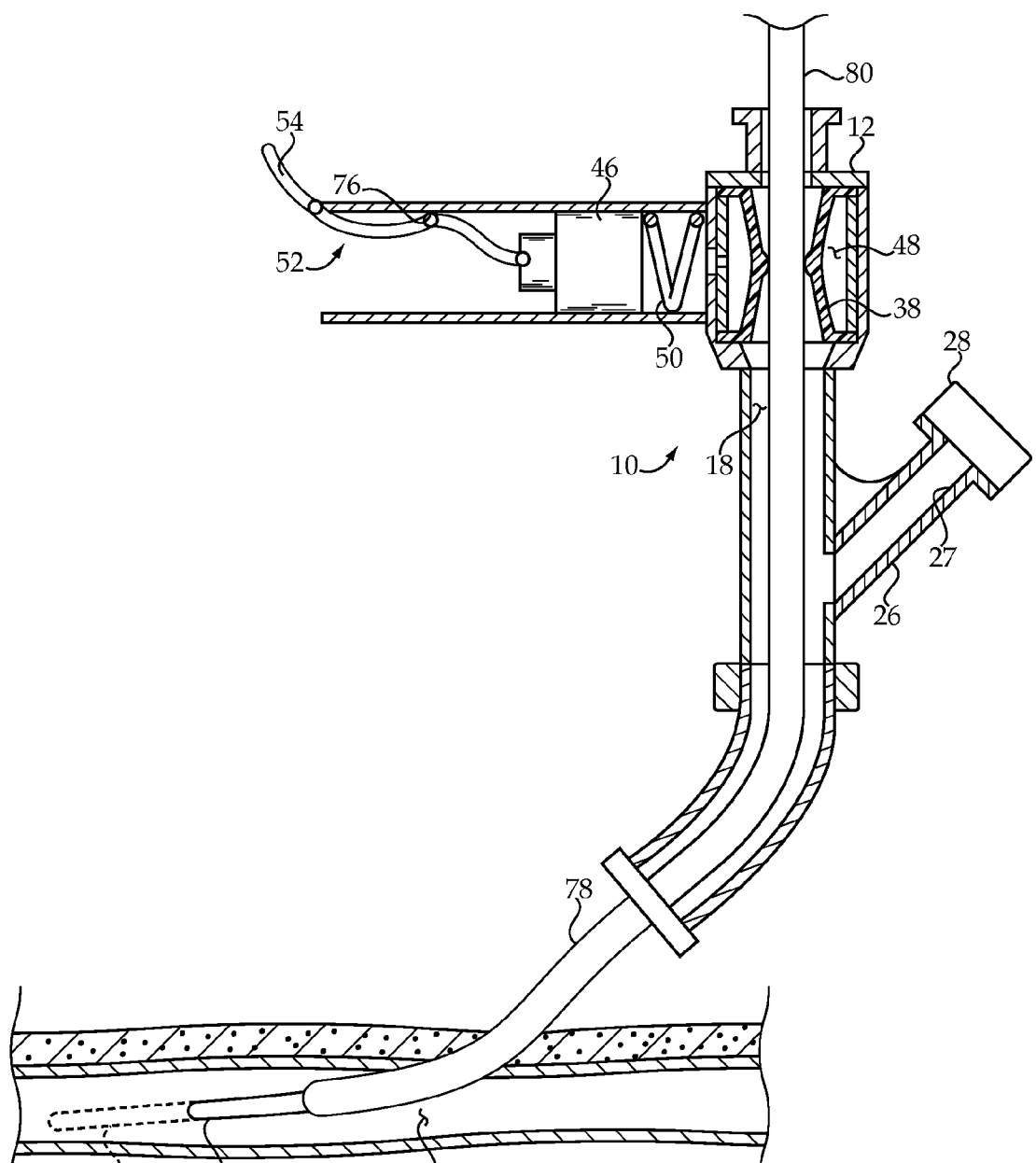
FIG. 3 is a sectioned side diagrammatic view of the mechanism of FIGS. 1 and 2, at one stage of a procedure according to one embodiment.

Referring to the drawings generally, but also now to FIG. 3, there is shown mechanism 10 as it might appear coupled with a conventional introducer 78 or the like, and where a medical device 80 is passed via through-bore 18 through mechanism 10, through introducer 78, and into a body lumen 300 such as a vein or artery in a patient. Seal 30 may include inwardly extending sealing elements 37 as shown in FIG. 1. When actuator 52 is used such that linkage 54 is moved to its advanced configuration contacting stop 76 and moving plunger 46 to displace fluid into clearance 32, sealing elements 37 may be moved via the inward deformation of seal 30 into sealing contact with medical device 80, approximately as shown in FIG. 3. Medical device 80 may include any elongate medical device such as a wire, a catheter, a sheath, a scope, or still another device.

Those skilled in the art will be familiar with the need for clinicians to often repeatedly seal in a hemostasis mechanism to prevent blood or other fluid backflow, unseal and adjust the position of a medical device passing through the hemostasis mechanism, and then reseal about the medical device. In certain procedures, with the assistance of radiography a clinician may gain initial access into a body lumen, and then inject liquid contrast agent to determine a position of a medical device, reposition the medical device, and then inject additional contrast agent or take another action. So-called power injections where liquid is injected under relatively high pressure are also well known. In any of these and still other cases, it will often be desirable to form a robust seal about a medical device to prevent the injected agent from flowing back out of a hemostasis mechanism, and instead be directed into the body lumen of interest. Mechanism 10 will typically be well-suited for such applications, and sidearm 26 can be used to accommodate a syringe, pump or another mechanism for delivering the injected fluid. Preventing backflow of blood even where no injection or other delivery of fluid such as gravity drips or infusion is taking place is also readily enabled by the present disclosure.

Figure 4:
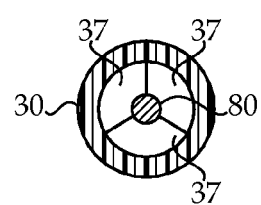
FIG. 4 is a sectioned view through a part of the mechanism as shown in FIG. 4.

Referring also now to FIG. 4, there is shown a sectioned view, through mechanism 10 and device 80 as it might appear either distally or proximally to the point at which sealing elements 37 engage medical device 80. In the illustrated embodiment, there is provided a total of three sealing elements 37 such that upon deforming seal 30 via fluid displaced with plunger 46, sealing elements 39 form a so-called tricuspid sealing pattern. Other sealing patterns may also fall within the scope of the present disclosure. Inward deformation of seal 30 in response to the displaced fluid will be used to provide circumferential sealing contact. When it is desirable to unseal mechanism 10 about medical device 80 for its repositioning, removal, or for another purpose, the deformation of seal 30 may be reversed via counter-rotating arms 56 and 60 such that the displaced fluid withdraws from clearance 32, the pressure in clearance 32 is reduced, and a natural tendency of seal 30 to return to its generally cylindrical shape draws sealing elements 37 out of sealing contact with medical device 80.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. Other aspects, features and advantages will be apparent upon an examination of the attached drawings and appended claims.

What is claimed is:

1. A hemostasis mechanism comprising:
a housing having an outer surface, and an inner surface defining a through-bore having a longitudinal axis;
a deformable seal extending circumferentially around the longitudinal axis and being positioned within the through-bore, and wherein a clearance extends between the deformable seal and the inner surface;
a plunger guided for translation within the housing from a first position to a second position to displace a fluid to the clearance, such that a fluid pressure in the clearance is increased to deform the deformable seal into sealing contact with a medical device within the through-bore;
an actuator for the plunger including a linkage having a first arm rotatable about a first axis relative the housing, and a second arm rotatable about a second axis relative the first arm and being coupled to the plunger, such that rotation of the first arm is converted via rotation of the second arm into translation of the plunger between the first and second positions; and
wherein the linkage at the second axis is positioned within the housing, and trapped to move between contact with a first stop within the housing and contact with a second stop within the housing.

2. The mechanism of claim 1 wherein the second arm is coupled to the plunger at a third axis; and
the first, second and third axes lie along a straight line when the linkage at the second axis is out of contact with both the first stop and the second stop.

3. The mechanism of claim 2 wherein the first axis has a fixed location relative the housing, and the second axis has a floating location relative the housing.

4. The mechanism of claim 3 wherein the first axis and the second axis are spaced a fixed distance apart.

5. The mechanism of claim 3 further comprising a biasing spring opposing translation of the plunger toward the second position.

6. The mechanism of claim 3 wherein the linkage further includes a first hinge coupling the first arm to the housing and defining the first axis, a second hinge coupling the second arm to the first arm and defining the second axis, and a third hinge coupling the second arm to the plunger and defining a third axis.

7. The mechanism of claim 6 wherein the linkage is in a retracted configuration corresponding to the first position of the plunger where the first, second, and third axes define a first included angle, and is adjustable to an advanced configuration corresponding to the second position of the plunger where the first, second and third axes define a second included angle.

8. The mechanism of claim 7 wherein the first angle and the second angle are opposite included angles, such that the linkage is cammed-over from the retracted configuration to the advanced configuration.

9. The mechanism of claim 8 wherein the housing includes the second stop contacted by the linkage in the advanced configuration.

10. The mechanism of claim 9 further comprising a biasing spring opposing translation of the plunger toward the second position, such that a biasing force of the biasing spring locks the linkage in the advanced configuration in contact with the stop.

11. A method of fluid sealing about a medical device in a hemostasis mechanism comprising the steps of:
   rotating arms of a linkage coupled with a plunger within a housing of the hemostasis mechanism, such that the plunger is translated in response to the rotation from a first position toward a second position;
   increasing fluid pressure within a clearance extending between a seal and the housing via fluid displaced via the translation of the plunger;
   deforming the seal into sealing contact with a medical device extending through the housing, in response to the increased fluid pressure; and
   the rotating step includes moving the linkage at an axis of rotation between the rotating arms that is positioned within the housing from contact with a first stop within the housing to contact with a second stop within the housing.

12. The method of claim 11 wherein the axis of rotation between the rotating arms is a second axis, and the linkage includes a first axis and a third axis; and
the rotating step includes moving the linkage past a point wherein the first, second and third axes lie along a straight line when moving from the first position to the second position.

13. The method of claim 12 further comprising a step of opposing the rotation of the arms via a biasing force of a biaser.

14. The method of claim 13 wherein the step of opposing includes opposing the rotation via a biasing force of a biasing spring transmitted to the linkage via the plunger.

15. The method of claim 13 further comprising a step of camming over the linkage via the rotation.

16. The method of claim 15 further comprising a step of locking the cammed-over linkage in an advanced configuration corresponding to the second position of the plunger via the biasing force.

17. The method of claim 15 wherein the step of rotating further includes rotating a first one of the arms about an axis having a fixed location relative the housing, and rotating a second one of the arms relative the first one about another axis having a floating location relative the housing.

18. The method of claim 17 wherein the step of deforming the seal further includes inwardly deforming the seal into circumferential sealing contact, and further comprising a step of reversing the deformation via counter-rotating the arms such that the displaced fluid withdraws from the clearance.

19. The method of claim 18 wherein the step of deforming further includes deforming the seal into a tricuspid pattern of sealing contact.

* * * * *